(12) United States Patent
Hiraoka

(10) Patent No.: US 7,830,275 B2
(45) Date of Patent: Nov. 9, 2010

(54) DEVICE FOR DISPLAYING OTHER SHIP TARGETS

(75) Inventor: Yasushi Hiraoka, Nishinomiya (JP)

(73) Assignee: Furuno Electric Company Limited, Nishinomiya (JP)

(*) Notice: Subject to any disclaimer, the term of this patent is extended or adjusted under 35 U.S.C. 154(b) by 208 days.

(21) Appl. No.: 11/922,676

(22) PCT Filed: Jun. 23, 2006

(86) PCT No.: PCT/JP2006/312617

§ 371 (c)(1),
(2), (4) Date: Dec. 21, 2007

(87) PCT Pub. No.: WO2006/137526

PCT Pub. Date: Dec. 28, 2006

(65) Prior Publication Data

US 2009/0079590 A1  Mar. 26, 2009

(30) Foreign Application Priority Data

Jun. 23, 2005  (JP)  ............................. 2005-183122

(51) Int. Cl.
    G08B 23/00  (2006.01)
    G01C 21/00  (2006.01)
    G01C 21/30  (2006.01)
(52) U.S. Cl. .................. 340/984; 701/202; 701/208
(58) Field of Classification Search ............ 340/984; 701/202, 208
    See application file for complete search history.

(56) References Cited

U.S. PATENT DOCUMENTS 4,706,090 A * 11/1987 Hashiguchi et al. ......... 342/41
5,202,829 A * 4/1993 Geier ....................... 701/215
5,404,135 A   4/1995 Janex et al.
5,426,436 A * 6/1995 Davis et al. ............... 342/182
6,658,349 B2 * 12/2003 Cline ....................... 701/207
7,016,772 B2 * 3/2006 Yanagi ..................... 701/21

FOREIGN PATENT DOCUMENTS

JP  61-93908 A  5/1986

(Continued)

Primary Examiner—Benjamin C Lee
Assistant Examiner—Andrew Bee
(74) Attorney, Agent, or Firm—Birch, Stewart, Kolasch & Birch, LLP

(57) ABSTRACT

An apparatus for displaying other ship targets is provided that displays the positions and detailed information concerning substantially all vessels present in a predetermined region around the own ship in a manner that is easy to grasp for the operator. A display screen includes Graphical Position Display Area 11, Target List Display Area 12 and Vessel Detail Information Display Area 13. A selected vessel of interest is displayed on Graphical Position Display Area 11 with Icon 102, and non-selected vessels are displayed by Icons 103 thereby making it possible to tell them apart. In conjunction with this, a portion of Target List Display Area 12 corresponding to the selected vessel is subjected to Emphasized Display 121, and the detailed information about the selected vessel is displayed in Vessel Detail Information Display Area 13. Here, when the operator switches the selected vessel in Graphical Position Display Area 11 or Target List Display Area 12, the display of the three areas changes in accordance with this operation, such that the selected vessel is subject to emphasized display and detailed display.

7 Claims, 9 Drawing Sheets

FOREIGN PATENT DOCUMENTS

| | | |
|---|---|---|
| JP | 6-131600 A | 5/1994 |
| JP | 10-84311 A | 3/1998 |
| JP | 11-160411 A | 6/1999 |
| JP | 2001-43500 A | 2/2001 |
| JP | 2001-273599 A | 10/2001 |
| JP | 2001-307299 A | 11/2001 |
| JP | 2002-157309 A | 5/2002 |
| JP | 2003-175889 A | 6/2003 |
| JP | 2004-355653 A | 12/2004 |

* cited by examiner

Fig. 7 ( B )
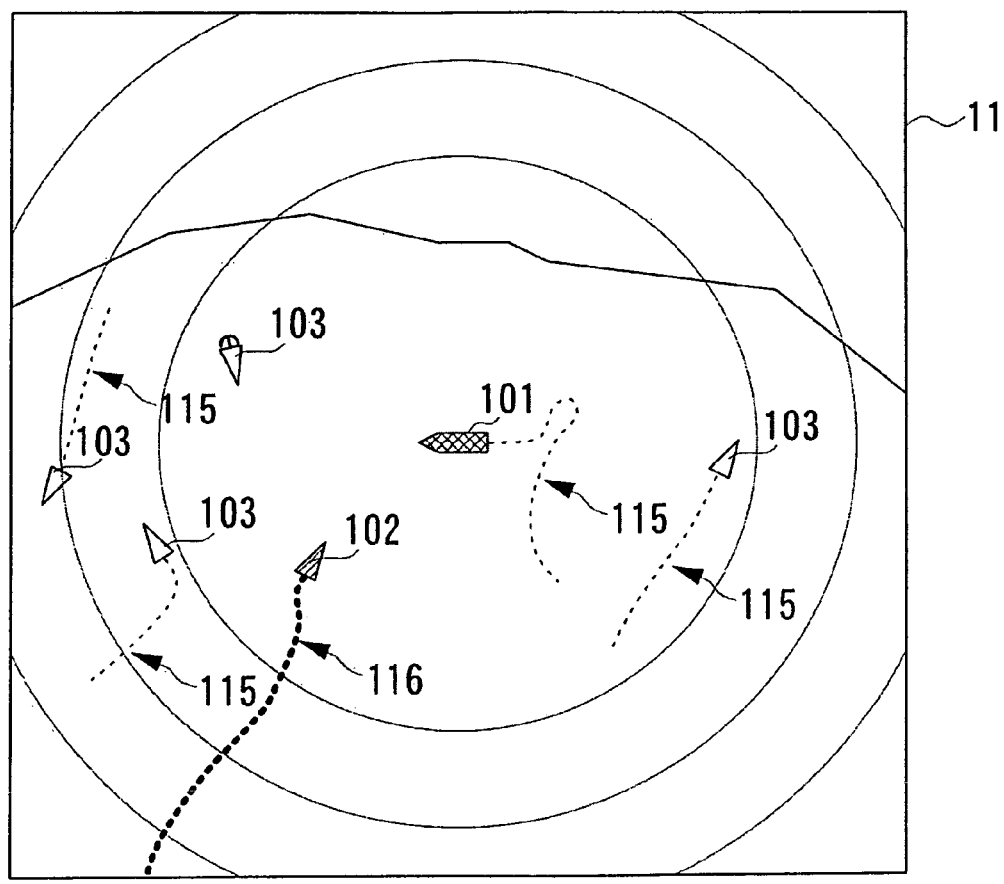

DEVICE FOR DISPLAYING OTHER SHIP TARGETS

TECHNICAL FIELD

The present invention relates to an apparatus for displaying other ship targets that displays the position of and information about ships within a predetermined range obtained by radio communication, and in particular to a display for displaying other ship targets that displays the position of and information about ships obtained by AIS and DSC.

BACKGROUND ART

Conventionally, the Universal Shipborne Automatic Identification System (referred to as "AIS" below) is used for collision avoidance and personal safety (see Patent Document 1 listed below).

AIS data includes, as static information, for example the vessel's Maritime Mobile Service Identity (MMSI), radio call sign and ship name, IMO number, ship length and width, ship type, and positions of the positioning system antennas, and as dynamic information, for example longitude and altitude, coordinated universal time, location accuracy, ground course, ground speed, heading, angular turning speed, and navigation status. As navigation-related information, the AIS data furthermore includes for example the vessel's draught, types of hazardous objects/substances on board, destination, and arrival time at destination, and it includes also navigational safety-related information. This AIS data is exchanged, as a vessel identification signal, by radio communication within a predetermined transmission distance. DSC has been in existence since before AIS, and includes a ringer for calling other ships, emergency navigation status, such as DISTRESS, and new instructions for transmit/receive signals by the base station.

An apparatus for transmitting/receiving AIS data includes by standard a display, namely a minimum keyboard display (MKD). Ordinarily the amount of displayed information displayed by this display is very sparse, in order to comply with the specifications for an extreme environment and to achieve a minimum display performance.

According to Patent Document 1, a conventional apparatus for displaying the various kinds of vessel information included in the AIS data employs the method of displaying on a screen of a radar apparatus information concerning each vessel according to the AIS data.

This apparatus compares the position information of other ships according to the AIS data with position information of other ships obtained by radar, displays the positions of specific ships for which there is a match with registered content on a nautical chart, and displays the detailed information concerning these specific ships in an independent display area separate from the nautical chart.

Patent Document 1: JP2001-281331A

DISCLOSURE OF THE INVENTION

Problem to be Solved by the Invention

However, with conventional MKDs, the display performance is poor, and they display only target lists listing little information, such as the MMSI, radio call name or some positional information. Therefore, the operator had to find the positional information of a vessel of interest from the target list and to visually confirm the position of the vessel of interest. Also when communicating by AIS with vessels very close nearby, the operator had to confirm, based on the visual results, the information such as the MMSI or radio call name of the corresponding vessel in the target list, and to perform various kinds of communication preparation actions.

Moreover, in the apparatus in Patent Document 1, only previously registered vessels are displayed on the nautical map and their detailed information is displayed, so that it is not possible to obtain information about substantially all vessels within a predetermined region around the own ship immediately and in real-time.

Also, in these conventional apparatuses, information about other ships is displayed, but the function for sending messages by AIS is provided separately, so that when editing messages from the displayed information, the editing of messages, such as the entering of the message recipient, has to be carried out from the beginning every time.

Furthermore, in these conventional apparatuses, there is no function for displaying the AIS or DSC reception timing, so that it was not possible to recognize at what time the present information has been obtained by AIS or DSC.

Accordingly, it is an object of the present invention to provide an apparatus for displaying other ship targets with which the positions of and detailed information about substantially all vessels within a predetermined region around the own ship can be displayed in a manner that is easy to grasp for the operator. Furthermore, it is an object of the present invention to provide an apparatus for displaying other ship targets with which the editing of messages to other ships with which communication is performed is simplified. Furthermore, it is an object of the present invention to provide an apparatus for displaying other ship targets with which AIS information received from other vessels, as well as the AIS transmission/reception and the DSC reception information of the own ship can be easily confirmed.

Means for Solving the Problems

An apparatus for displaying other ship targets according to the invention comprises a processor for obtaining detailed information including at least a name and position information of each vessel by analyzing vessel information that is transmitted and received by radio communication, and a display for displaying the detailed information, and the display further comprising a target list display which is configured to list information about each vessel, and a graphical position display which is configured to mark the surface position of each vessel based on the position information. The display updates the target list display and the graphical position display simultaneously and in association with one another based on the detailed information obtained from the processor.

With this configuration, when AIS radio communication signals are received, these signals are demodulated with an AIS receiver to obtain AIS data. The processor acquires detailed information about each ship by analyzing the obtained AIS data, and forwards this information to the display. The display is provided with a target list display, which corresponds to an area displaying target list and a graphical position display, which corresponds to an area in which the surface positions of the various vessels are marked, plotting their positions on a nautical chart. The display is successively updated, and each time the received AIS data is acquired, the target list display and the graphical position display are simultaneously updated. That is to say, the vessels displayed on the graphical position display as well as the vessels and their accompanying detailed information listed in the target list display are displayed in association with each other.

Moreover, an apparatus for displaying other ship targets according to the invention may be characterized in that it further comprises a human/machine interface for enabling an operation input, and that, when a mark representing a specific vessel on the graphical position display is selected or a portion of the target list display corresponding to the specific vessel is selected with the human/machine interface, the specific vessel on the graphical position display and the specific vessel portion in the target list display are displayed in an emphasized manner.

With this configuration, as noted above, the information concerning each vessel displayed with the target list display and the positional information of each vessel displayed in the graphical position display are associated with each other, so that when a specific vessel is selected with the human/machine interface in either one of the two, the portion concerning the corresponding specific vessel in the two displays is displayed in an emphasized manner, that is, in a manner that is different from the portions concerning the other (non-selected) vessels.

Moreover, an apparatus for displaying other ship targets according to the invention may be characterized in that the display comprises a detailed vessel information display for displaying the detailed information, and the detailed vessel information display is configured to display detailed information about the specific vessel selected with the human/machine interface.

With this configuration, detailed information about the selected specific vessel is displayed, in the detailed vessel information display. That is to say, when a corresponding vessel portion is selected in either the target list display or the graphical position display as noted above, detailed information about the selected vessel is displayed in the detailed vessel information display in accordance with the selection.

Moreover, an apparatus for displaying other ship targets according to the invention may be characterized in that, by selecting a mark representing a specific vessel on the graphical position display or by selecting a portion of the target list display corresponding to the specific vessel with the human/machine interface for performing a message preparation operation, the display is configured, to display a message editor box for editing a message to the specific vessel.

With this configuration, by selecting a portion corresponding to a specific vessel in one of the displays for performing an operation corresponding to message editing, an editing screen(box) for editing a message to the specific vessel, in which the recipient is already selected, is displayed. Then, when the message is edited and a send operation is carried out, the messages sent out.

Moreover, an apparatus for displaying other ship targets according to the invention may be characterized in that the processor is configured to detect a reception timing at which information from a vessel has been received by radio communication, and the display is configured to display the marks in an emphasized manner on the graphical position display for the corresponding vessels in accordance with the reception timing.

With this configuration, the processor carries out an analysis of the AIS data and the reception timing of that AIS data is detected. Based on this reception timing and the vessel information, the display is configured to display the corresponding vessels on the graphical position display in an emphasized manner. Thus, the timing at which AIS messages have been received from the various vessels is expressed in the graphical position display.

Moreover, an apparatus for displaying other ship targets according to the invention may be characterized in that, when the processor obtains through AIS or DSC radio communication an AIS navigation status of a vessel or a DSC distress/emergency notification, the display is configured to display at least a status mark representing the navigational status at the mark of the corresponding vessel on the graphical position display.

With this configuration, when a navigation status or a distress/emergency call included in the AIS data or DSC data is acquired, status marks are appended to the marks of the vessels displayed on the graphical position display. Thus, the navigation status of each vessel can be recognized visually.

Moreover, an apparatus for displaying other ship targets according to the invention may be characterized in that it further comprises a memory for storing vessel information for a certain period of time, and when a specific vessel is selected with the human/machine interface, the display is configured to display the ship trail of the corresponding specific vessel on the graphical position display in an emphasized manner.

With this configuration, by displaying the trail for the selected vessel in an emphasized manner, it can be visualized from where the vessel of interest has come.

EFFECTS OF THE INVENTION

In accordance with the invention, the positions of all vessels within a predetermined region including the own ship as well as their vessel information can be easily visualized, and the position of a vessel of interest as well as its detailed information can be easily selected from among a large number of vessels, and displayed. This is advantageous for safe navigation.

Moreover, in accordance with the invention, by merely selecting a vessel of interest and performing a simple operation, it is possible to edit and send a message to that vessel.

Moreover, in accordance with the invention, it is possible to easily visualize the AIS or similar radio communication state for each vessel, so that it is possible to recognize whether the vessels on the display are indeed constantly communicating by radio communication. Thus, it can be recognized whether the currently displayed position and detailed information have been recently updated.

INDEX TO THE REFERENCE NUMERALS

1—processor,
2—AIS/DSC—transmitter,

3—AIS receiver,
4—DSC receiver,
5—display,
6—antenna,
7—human/machine interface,
8—memory,
11—graphical position display area,
12—target list display area,
13—detailed vessel information display area,
14—AIS message editing area,
101—icon for own ship,
102—icon for vessel of interest,
103—icon for non-selected vessel,
110—flashing/blinking display,
111—send message number display area,
112A, 112B—navigation status symbol,
115—ordinary trail display,
116—emphasized trail display

BEST MODE FOR CARRYING OUT THE INVENTION

Referring to FIGS. 1 to 7, the following is an explanation of an apparatus for displaying other ship targets according to an embodiment of the present invention.

Figure 1:
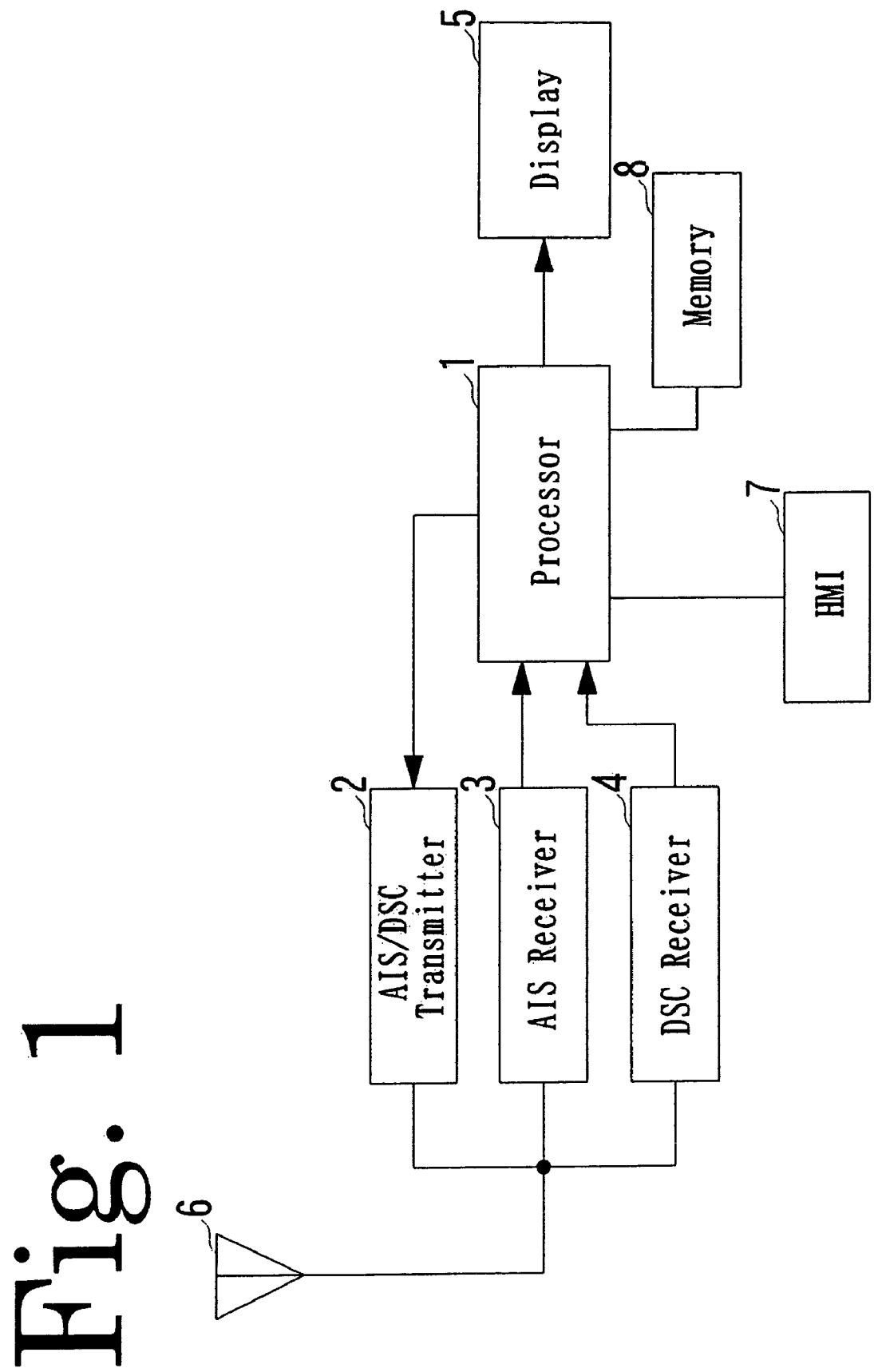
FIG. 1 is a block diagram showing the general configuration of an apparatus for displaying other ship targets according to an embodiment of the present invention.

FIG. 1 is a block diagram showing the general configuration of an apparatus for displaying other ship targets according to this embodiment.

The apparatus for displaying other ship targets according to this embodiment includes Processor 1, AIS/DSC Transmitter 2, AIS Receiver 3, DSC Receiver 4, Display 5, Antenna 6, Human/machine interface 7 and Memory 8.

AIS Receiver 3 is ordinarily in a receiver mode, and receives AIS communication signals in TDMA communication format through Antenna 6. AIS Receiver 3 generates AIS data by demodulating the AIS communication signals received from other ships, and outputs the AIS data to Processor 1. AIS Receiver 3 also receives and demodulates the feedback signal of the AIS communication signal transmitted from AIS/DSC Transmitter 2, generates AIS data and outputs this AIS data to Processor 1.

Also DSC Receiver 4 is ordinarily in a receiver mode and receives DSC communication signals through Antenna 6. DSC Receiver 4 demodulates the received DSC communication signal and generates DSC data, which it outputs to Processor 1.

When AIS data is input into Processor 1, Processor 1 analyzes this data, and obtains AIS messages with each vessel's static information, dynamic information, navigation-related information and navigational safety-related information. When DSC data is input into Processor 1, Processor 1 analyzes this data, and obtains DSC messages with emergency information, such as a DISTRESS signal.

Processor 1 generates an AIS message and a DSC message that are sent out from the own ship, and at a timing set in advance in accordance with the local transmission timing, it forwards the AIS messages to AIS/DSC Transmitter 2. Furthermore, it forwards the DSC message to AIS/DSC Transmitter 2 at intervals other than the AIS transmitting/receiving interval, in accordance with a command from the base station.

AIS/DSC Transmitter 2 modulates the received AIS message onto a transmission signal of a predetermined frequency, and transmits it out through Antenna 6 at a reserved local transmission timing. AIS/DSC Transmitter 2 also modulates the received DSC message onto a transmission signal of a predetermined frequency, and transmits it out through Antenna 6 at a timing at which no AIS transmission or reception is performed.

Processor 1 controls the various components of the apparatus in accordance with processing instructions that are entered through Human/machine interface 7.

Processor 1 carries out the above-described transmitting/receiving processes, obtains various kinds of information constituting the AIS messages and DSC messages received from other vessels, and in addition to outputting it with Display 5, stores this information in Memory 8.

Display 5 includes a display screen having a predetermined resolution, and an image data generator generating image data that is output on this display screen. Based on the various kinds of information received from Processor 1, the image data generator of Display 5 generates the image data in accordance with the processing method explained in detail below, and outputs the image on the display screen.

(1) Information Display Function

Figure 2:
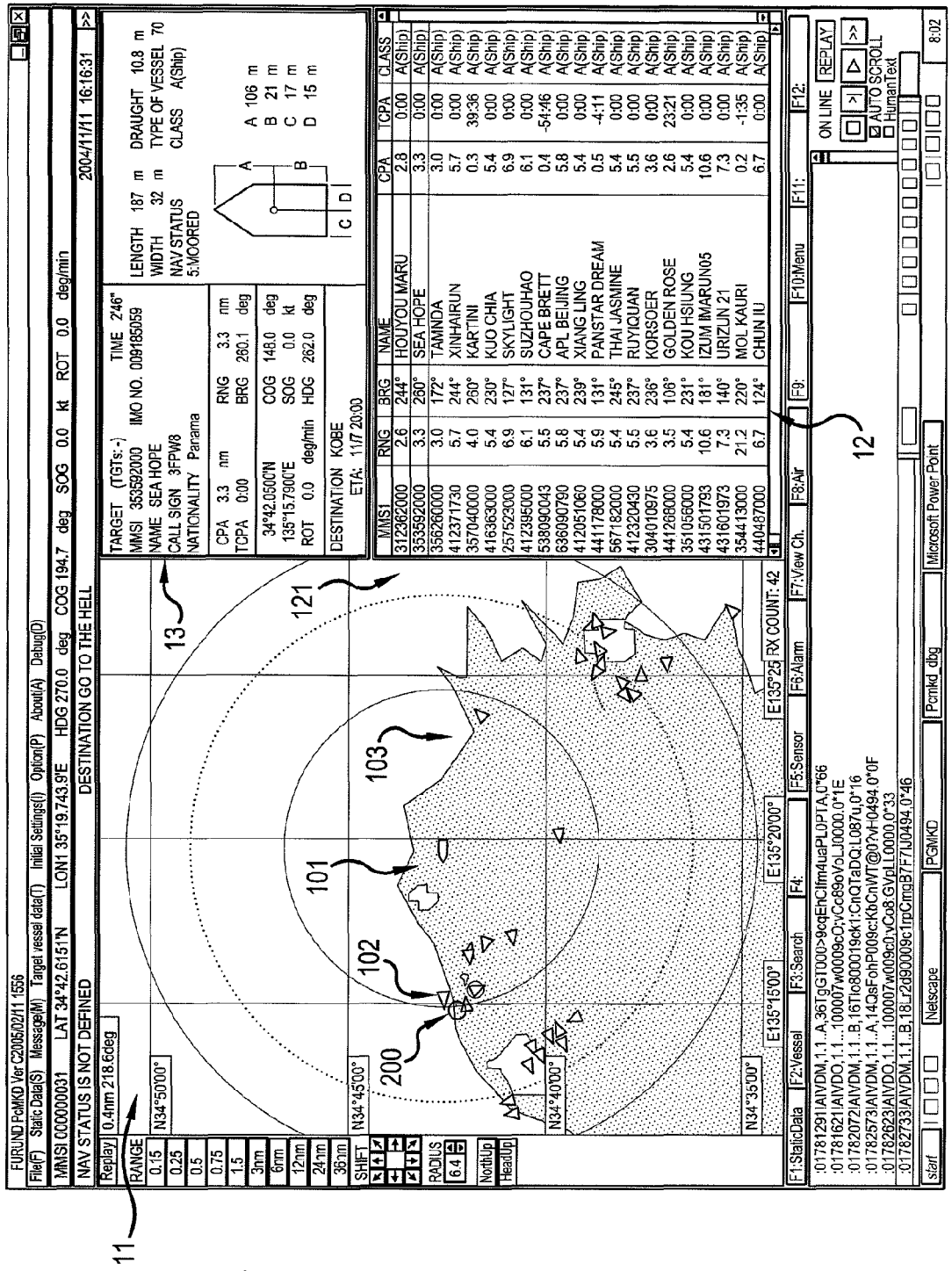
FIG. 2 is a diagram showing an example of a display screen of the apparatus for displaying other ship targets according to an embodiment of the present invention.

FIG. 2 is a diagram showing an example of a display screen of the apparatus for displaying other ship targets according to the present embodiment.

As shown in FIG. 2, the display screen includes Graphical Position Display Area 11, which displays as icons the positions of each vessel on a nautical chart stored in advance, Target List Display Area 12, which displays a list with information regarding the vessels whose AIS messages have been received, and Vessel Detail Information Display Area 13, which displays detailed information obtained by AIS messages.

Graphical Position Display Area 11 plots the own ship approximately at the center of the nautical chart stored in advance, and displays it as Icon 101 of an approximate vessel shape (a pentagon in which one vertex corresponds to the heading direction). Based on the position information of the various vessels obtained with Processor 1, the various vessels are plotted and displayed as Icons 102, 103 of specific shapes (in FIG. 2, triangles in which one vertex corresponds to the heading direction). It should be noted that Graphical Position Display Area 11 displays all vessels whose AIS messages could be obtained as Icons 102 or Icons 103.

Icon 102 is an icon representing a vessel that has been selected with Human/machine interface 7, and is displayed in a color that is different to that of the other vessels, that is, in a color that is different to that of Icons 103 for the non-selected state. Here, Human/machine interface 7 is a keyboard or a mouse with which the apparatus is equipped. In the case of a keyboard, the other vessel of interest is selected by selecting the icons representing the other ships successively through a specific key operation. In the case of a mouse, on the other hand, the other vessel of interest is selected by clicking while pointing the pointer at the icon of the other vessel of interest.

Since only Icon 102 of the selected other vessel of interest is displayed in a color that is different to that of the Icons 103 of the remaining other vessels, the other vessel of interest can be easily distinguished visually from the other vessels.

Target List Display Area 12 lists the general information for each vessel obtained by Processor 1, and through an analysis of the AIS messages, the information of the vessels can be displayed in order from the start (from the top of the list). For example, in the example of FIG. 2, the necessary information for identifying each vessel, such as the MMSI or the ship's name or the like, is displayed in brief.

Of the information about each vessel listed in Target List Display Area 12, the information corresponding to Icon 102 in Graphical Position Display Area 11, that is, the information relating to the vessel of interest, is subject to Emphasized Display 121 in a color different to that of the information for the other vessels.

Vessel Detail Information Display Area 13 displays detailed information about the vessel that is subject to Emphasized Display 121 in Target List Display Area 12. This detailed information includes for example the static information and the dynamic information contained in the AIS message analyzed by Processor 1. In the example in FIG. 2, the various kinds of information contained in the static information, the various kinds of information contained in the dynamic information and the various kinds of information contained in the navigation-related information are displayed.

Graphical Position Display Area 11, Target List Display Area 12 and Vessel Detail Information Display Area 13 are associated with each other, and when Icon 102 of Graphical Position Display Area 11 is changed to another vessel, also the vessel for which the display is subject to Emphasized Display 121 in Target List Display Area 12 is changed accordingly. Furthermore, in accordance with this change, also in Vessel Detail Information Display Area 13, the display is changed to the vessel corresponding to the newly changed Icon 102, that is, to the detailed information for the vessel with Emphasized Display 121 in Target List Display Area 12.

This switching of the vessel of interest is also possible by changing Emphasized Display 121 in Target List Display Area 12. More specifically, the position of the Emphasized Display 121 in Target List Display Area 12 can be changed using Human/machine interface 7. For example, if Human/machine interface 9 [=>7] is a mouse, this can be achieved by pointing the pointer at the data row of the new vessel of interest and clicking. Thus, Emphasized Display 121 moves to the vessel information row at the clicked position, and accordingly, also Icon 102 of Graphical Position Display Area 11 is switched. In accordance with this change, the display of the detailed information about the vessel with Emphasized Display 121 in the newly changed Target List Display Area 12, that is, about the vessel corresponding to Icon 102 is switched in Vessel Detail Information Display Area 13.

With this configuration, an operator can easily obtain general information and detailed information about vessels with Target List Display Area 12 and Vessel Detail Information Display Area 13 by selecting a vessel whose detailed information he or she wishes to view, in accordance with the relative surface positions obtained with Graphical Information Display Area 11. Accordingly, it is possible to greatly reduce the burden of operation and identification for the operator when obtaining for example the detailed information about a ship that is close to one's own ship on the nautical chart, or when obtaining the radio call sign and the name of a ship using the AIS message transmission.

Moreover, by seeking and selecting a vessel of interest from the ship names in Target List Display Area 12, it is easily possible to identify its relative position on the nautical chart (surface position), that is, in which direction and at what distance from one's own ship the other vessel is located. Thus, it is possible to greatly reduce the burden of operation and identification for the operator, when looking for fellow ships of the same trade.

(2) AIS Text Message Sending Function

The following is an explanation of the processing of an apparatus for displaying other ship targets according to the present embodiment when sending an AIS text message as noted above.

Figure 3:
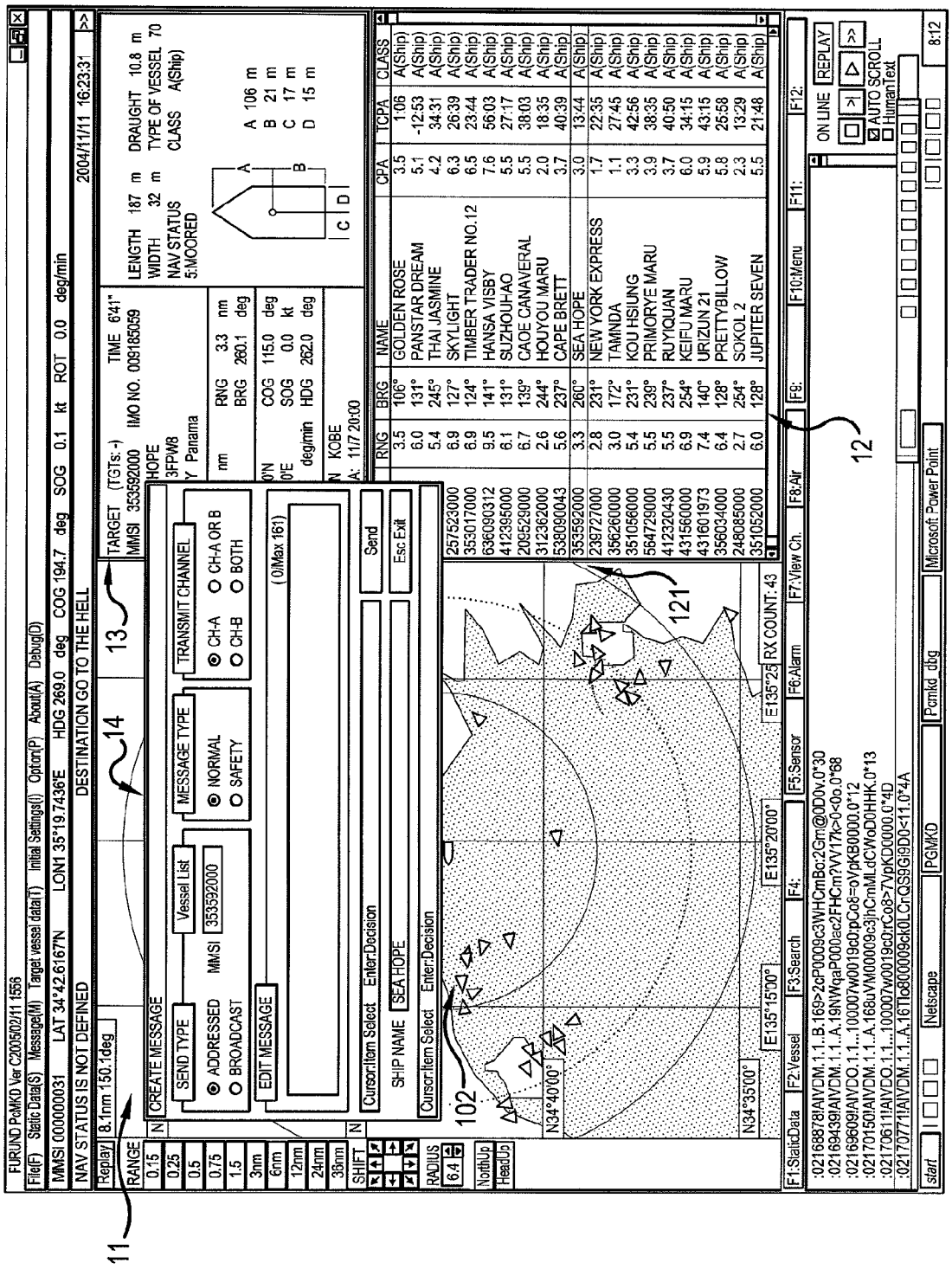
FIG. 3 is a display screen of Display 5 in a state in which AIS Text Message Editing Area 14 is popped up.

FIG. 3 is a display screen of Display 5 in a state in which AIS Text Message Editing Area 14 is popped up.

As noted above, when a predetermined AIS text message preparation operation is carried out with Human/machine interface 7 in a state in which a vessel of interest is selected, AIS Text Message Editing Area 14 with the MMSI of the selected vessel written in advance is displayed on the display screen. More specifically, in a message preparation operation, first, the vessel of interest is selected by selecting an icon on Graphical Position Display Area 11 or by selecting the portion of Target List Display Area 12 corresponding to that vessel. Then, after the selection operation, a right click followed by a selection from a pull-down menu or a double click are performed, if a mouse is used for example.

Using Human/machine interface 7, the operator writes a message to be sent to the vessel of interest into the comment field of the newly displayed AIS Text Message Editing Area 14, and selects a start transmission (SEND) tab. Processor 1 performs the above-described AIS transmission process in response to this operation. Then, at the local transmission timing, the edited AIS text message is sent out, addressed to the vessel of interest. By using this configuration and processing method, it is not necessary to enter the MMSI when editing or sending the AIS text message, so that the AIS text message can be easily edited. Furthermore, since the operator does not have to enter the MMSI, errors in entering the MMSI can be prevented. Moreover, it is possible to confirm the vessel of interest from the target list, from the relative surface position, or from the detailed information, so that it is possible to prevent errors in the selection of the vessel of interest, that is, of the vessel to which a comment or message is to be sent.

(3) Target Vessel Searching Function

The following is an explanation of a method for searching a vessel of interest when the MMSI or radio call sign is known.

While vessels are displayed in Target List Display Area 12, the operator can search a vessel to which information is to be sent. For this, the operator enters numbers or letters using Human/machine interface 7.

When a number is entered with Human/machine interface 7, Processor 1 performs Emphasized Display 121 with respect to the vessel information for which the number at the start of the MMSI matches the entered number and that is furthest to the top in the target list. Then, when further numbers are entered, the second and third digits from the start of the MMSI are successively matched up. Thus, the operator can easily confirm the general information and position (numerical) of the vessel of interest from the MMSI. The result is also reflected in the other display areas (in Graphical Position Display Area 11 and Vessel Detail Information Display Area 13). Thus, the operator can easily obtain, from the MMSI, the detailed information and the position on the nautical chart of the vessel of interest.

On the other hand, when letters are entered into Human/machine interface 7, Processor 1 performs Emphasized Display 121 with respect to the vessel information for which the letter at the start of the radio call name matches the entered letter and that is furthest to the top in the target list. Then, when further letters or numerals are entered, the second and third digits from the start of the radio call name are successively matched up. Thus, the operator can easily confirm the general information and position (numerical) of the vessel of interest from the radio call name. The result is also reflected in the other display areas (in Graphical Position Display Area 11 and Vessel Detail Information Display Area 13). Thus, the operator can easily obtain, from the radio call name, the detailed information and the position on the nautical chart of the vessel of interest.

(4) AIS Reception Timing Display Function

The following is an explanation of a method for displaying the reception timing of AIS data from various vessels including the own vessel.

Figure 4:
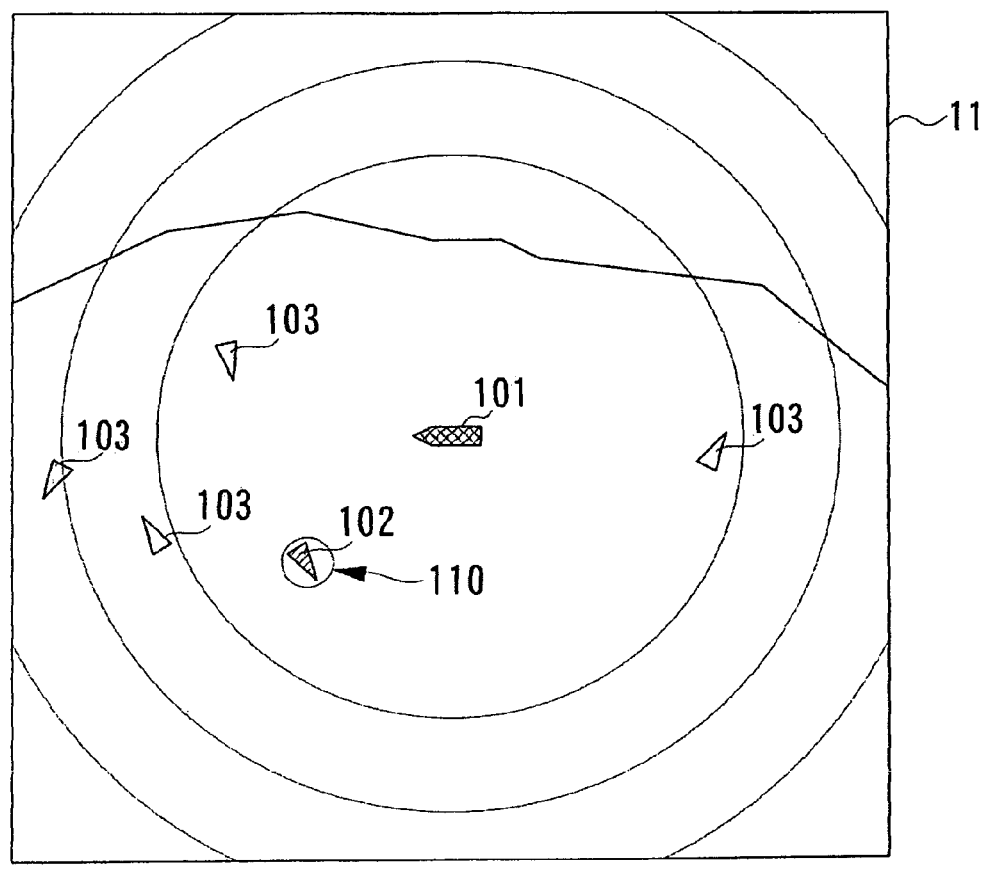
FIG. 4 shows schematic enlarged views of Graphical Position Display Area 11 illustrating an AIS reception timing display function.
Figure 4:
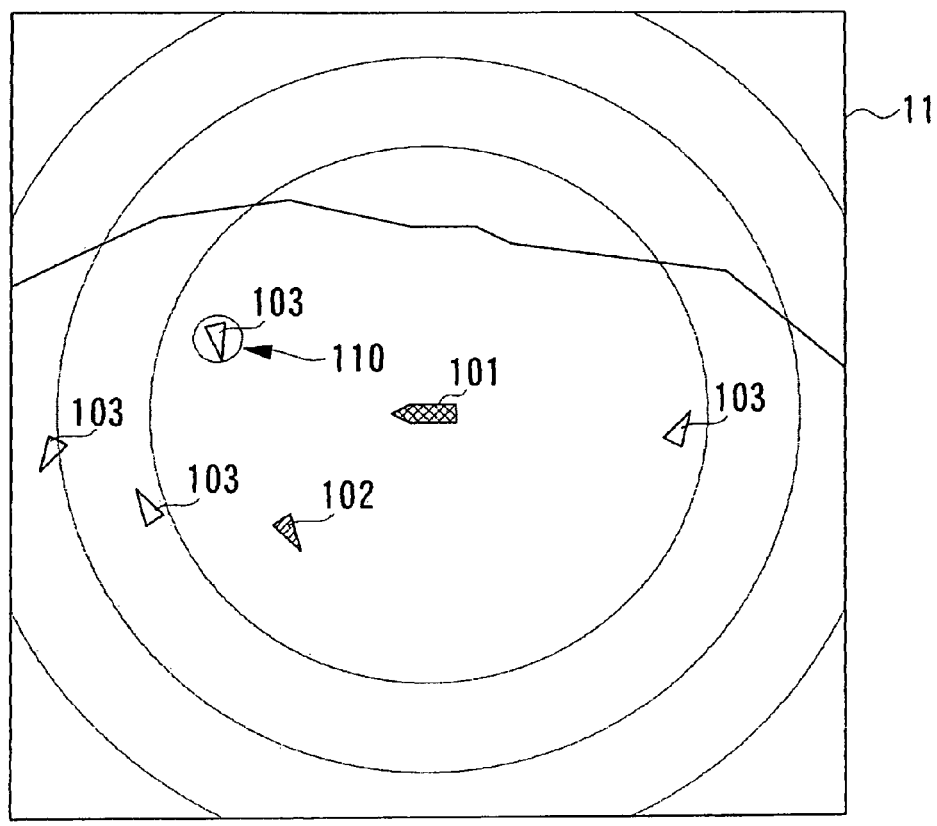

FIG. 4 shows schematic enlarged views of Graphical Position Display Area 11, with FIGS. 4(A) and 4(B) taken at different times.

When AIS data is entered from the AIS Receiver 3, Processor 1 performs a packet check and analyzes the AIS message. In doing so, Processor 1 generates AIS reception timing data and associates it with the vessel information obtained by the analysis. In accordance with the entered vessel information and AIS reception timing data, Display 5 performs a Flashing or Blinking Display 110 around the icon of the corresponding vessel in Graphical Position Display Area 11 (in FIG. 4(A), Icon 102 of the vessel of interest, and in FIG. 4(B), Icon 103 of a non-selected vessel). This processing is carried out every time AIS data is received, and the Flashing (Blinking) Display 110 moves in the order in which the AIS data is received (for example, FIG. 4(A)→FIG. 4(B)).

Thus, by simply viewing the Vessel Icons 102, 103 in Graphical Position Display Area 11, the frequency of the reception timing of AIS messages from the various vessels, including the vessel of interest, can be easily confirmed. It should be noted that this frequency of the reception timing also can be confirmed by displaying in the Vessel Detail Information Display Area 13 shown for example in FIG. 2 the time that has passed since the previous AIS message has been received. As a result, the operator can confirm whether an AIS message has actually been sent from each vessel and when it has been received by own vessel, and furthermore, the operator can confirm whether the positions of the other vessels are the most recent ones, which is advantageous for safe navigation.

It should be noted that the flashing (blinking) display can be performed not only with respect to the other vessels, but also on the own vessel. Moreover, by similarly letting the display format of the vessel of interest be different from the display format of the other vessels, it is possible to display the vessel of interest and the information concerning that vessel of interest by emphasized display.

Figure 5:
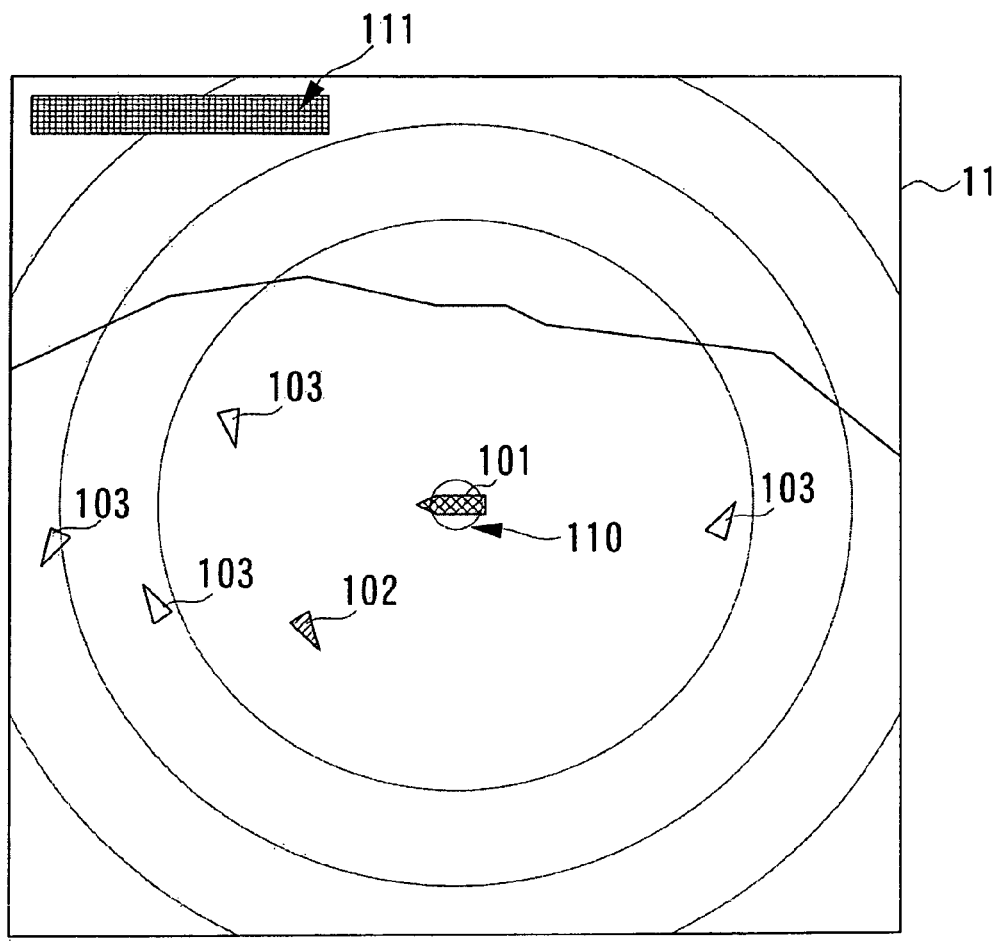
FIG. 5 is a schematic enlarged view of Graphical Position Display Area 11 in which the own vessel is flashing.

FIG. 5 is a schematic enlarged view of Graphical Position Display Area 11 in which the own vessel is flashing.

When AIS data is entered from the AIS Receiver 3, Processor 1 performs a packet check and analyzes the AIS message. In doing so, Processor 1 generates AIS reception timing data and associates it with the vessel information obtained by the analysis. Furthermore, Processor 1 obtains information that is unique to the vessel, such as the MMSI of the analyzed AIS message, and if this information matches with the unique information of the own station, such as the MMSI, it is judged that the received AIS data is from the own station. Then, the message number is obtained from the received text of AIS Receiver 3.

In accordance with the entered vessel information and AIS reception timing data, Display 5 performs Flashing or Blinking Display 110 around the corresponding Icon 101 of the own ship in Graphical Position Display Area 11 (of the own ship shown at the center in FIG. 5). Furthermore, Display 5 displays the entered send message number in Send Message Number Display Area 111.

Thus, the operator can confirm easily and accurately the frequency of the AIS data transmission timing and the send message number of the own ship, by simply viewing Icon 101 of the own vessel in Graphical Position Display Area 11 and Send Message Number Display Area 111.

It should be noted that in the foregoing explanations, the flashing and blinking display is performed only when AIS data is received, but among AIS messages, there are messages with static information including general vessel information and messages that merely notify the position, and there are cases where a DSC message includes distress or emergency information of the vessel in question. It is also possible to mark this information by flashing (blinking) or by using different colors. Thus, it is possible to display the result of the analysis of the AIS message from another vessel or the like in even more detail and more easily to understand.

(5) Navigation Status and Emergency Navigation Status Display Function

The following is an explanation of a method for displaying the navigation status and the emergency navigation status of other vessels.

Figure 6:
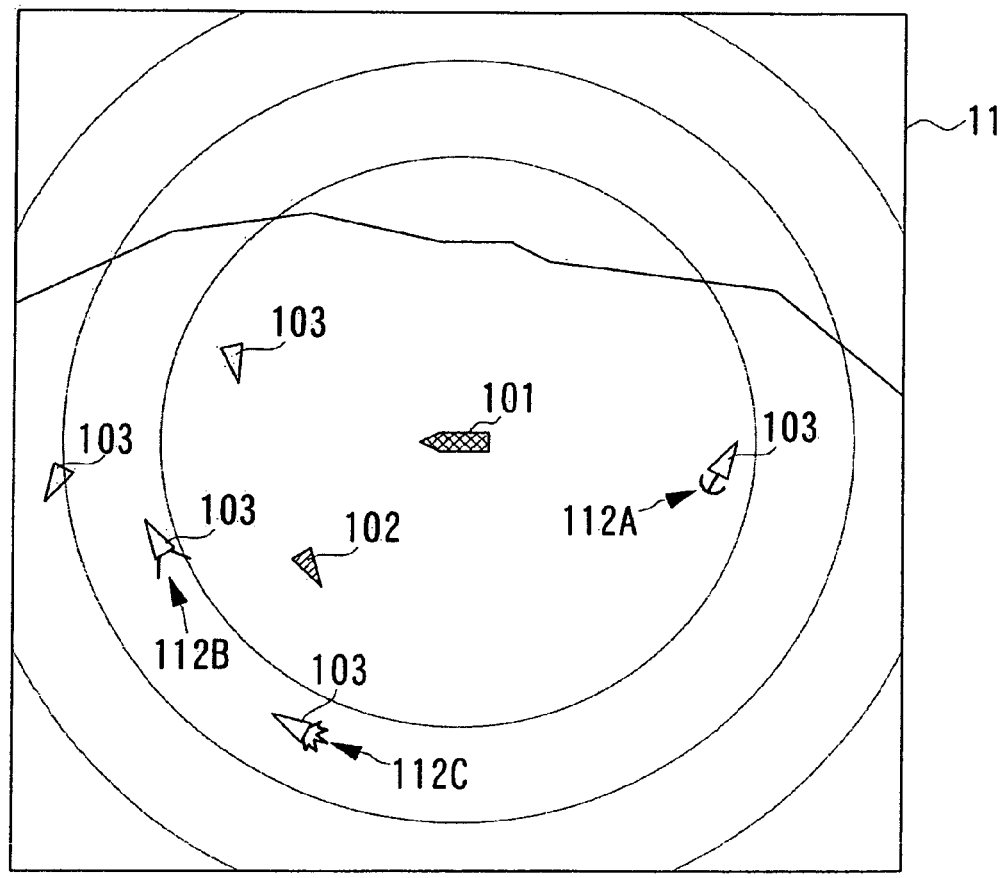
FIG. 6 is a schematic enlarged view of Graphical Position Display Area 11 illustrating a navigation status and emergency state display function.

FIG. 6 is a schematic enlarged view of Graphical Position Display Area 11

There are cases in which an AIS message includes the navigation status of the vessel where a transmission originates, and there are cases in which a DSC message includes distress/emergency information about the vessel in question.

When Processor 1 obtains a navigation status such as MOORE or ANCHOR from an AIS message, Display 5 displays Navigation Status Symbols 112A or 112B, appending them to the Icons 103 of the corresponding vessels. Furthermore, when the Processor 1 obtains distress/emergency information, such as a DISTRESS signal, by analyzing the DSC data demodulated by DSC Receiver 4, Display 5 displays Emergency Information Symbol 112C, appending it to Icon 103 of the corresponding vessel. Here, if the navigation status or distress/emergency information is detected also for Icon 102 of the vessel of interest, Navigation Status Symbols 112A or 112B or Emergency Information Symbol 112C may also be displayed by appending them accordingly.

With this configuration, the operator can easily identify the navigation status and the distress/emergency information for each vessel by simply viewing the Vessel Icons 102, 103 on Graphical Position Display Area 11. As a result, this can be advantageous for safe navigation and may be helpful for marine rescue operations.

As explained previously, an example was given, in which the navigation status and the distress/emergency information for each vessel are displayed by icons, but it is also possible to use a text display format, in which letters are displayed, such as "A": ANCHOR; "D": DISTRESS; "M": MOORE.

(6) Ship Trail Display Function

The following is an explanation of a method for displaying the ship's trail for each vessel, including the own ship.

Figure 7:
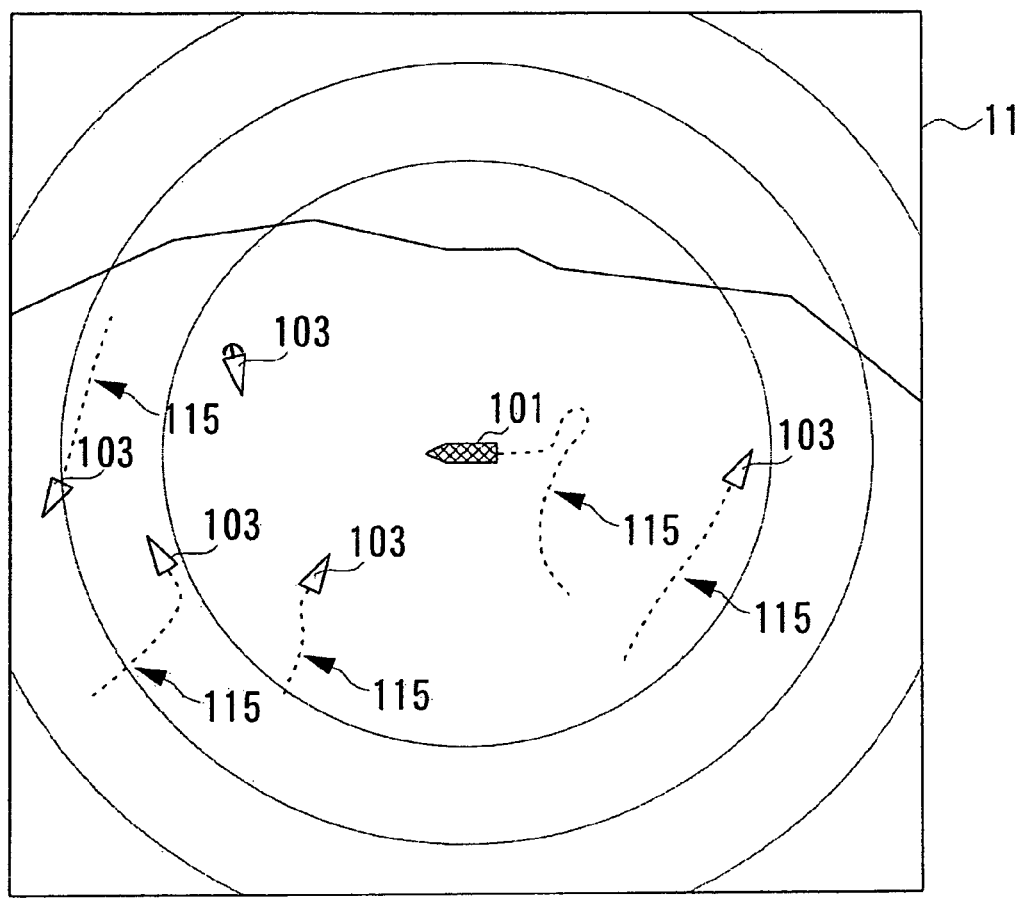
FIG. 7 is a schematic enlarged view of Graphical Position Display Area 11 illustrating a trail display function.

FIG. 7 is a schematic enlarged view of Graphical Position Display Area 11. FIG. 7(A) illustrates the case that no vessel within the display area is selected, and FIG. 7(B) illustrates the case that a vessel within the display area is selected.

Ordinarily, Ship Trails 115 of each vessel, regardless of whether it is the own ship or another ship, are displayed in Graphical Position Display Area 11 (FIG. 7(A)). Ship Trails 115 of this ordinary display are ship trails starting at a predetermined period of time ago from the present time, which is set in accordance with the storage capacity of Display 8 [=>Memory 8].

Here, when the operator selects a vessel of interest using Human/machine interface 7, the icon of the selected vessel changes from Condition 103 to Condition 102. Processor 1 recognizes this selection process, reads out the past position information of the corresponding vessel stored in Memory 8 and forwards it to Display 5. Display 5 appends to Icon 102 of the vessel of interest an emphasized Ship Trail 116 of a style (bold in FIG. 7) that is different to that of the ordinary Ship Trail 115. In this situation, the positions for times that are further in the past than those stored locally are also given to Display 5, so that the emphasized Ship Trail 116 is displayed in accordance with the position information given to Display 5.

Thus, by selecting the vessel of interest, the operator can observe the ship trail of at least that vessel to the extent possible in accordance with the capacity of the Memory 8.

It should be noted that during this display, it is also possible to display on the Graphical Position Display Area 11 the time that has passed from the nearest AIS reception timing from the vessel of interest (the vessel of Icon 102). Thus, the operator can easily confirm whether the position and the trail that are displayed are based on recent data or based on old data.

The invention claimed is:

1. An apparatus for displaying other ship targets comprising:
   a processor for obtaining detailed information including at least a name and position information of each vessel by analyzing vessel information that is transmitted and received by radio communication at specified timing intervals; and
   a display for displaying the detailed information, the display including:
      a target list display which is configured to list information about each vessel; and
      a graphical position display which is configured to mark the surface position of each vessel based on the received position information, wherein
   the target list display and the graphical position display are updated simultaneously and in association with one another based on the detailed information obtained from the processor,
   the processor is configured to detect when detailed information from a vessel corresponding to a mark displayed on the graphical position display has been received by radio communication, and
   when receipt of detailed information is detected by the processor, the display is configured to emphasize the display of the mark corresponding to the received detailed information.

2. The apparatus for displaying other ship targets according to claim 1,
   further comprising a human/machine interface for enabling an operation input;
   wherein a specific vessel on the graphical position display and the specific vessel portion in the target list display are displayed in an emphasized manner when a mark representing the specific vessel on the graphical position display is selected or a portion of the target list display corresponding to the specific vessel is selected with the human/machine interface.

3. The apparatus for displaying other ship targets according to claim 1 or 2, wherein the display further comprises a detailed vessel information display which is configured to display detailed information about a specific vessel selected with the human/machine interface.

4. The apparatus for displaying other ship targets according to claim 2, wherein the display is further configured to display a message editor box for editing a message to a specific vessel by selecting a mark representing the specific vessel on the graphical position display or by selecting a portion of the target list display corresponding to the specific vessel with the human/machine interface for performing a message preparation operation.

5. The apparatus for displaying other ship targets according to claim 1, wherein the display is configured to display the marks in an emphasized manner by performing a flashing or blinking display around the mark of a corresponding vessel on the graphical position display for the corresponding vessels every time information from a vessel is received.

6. The apparatus for displaying other ship targets according to claim 1, wherein the display is configured to display at least a status mark representing the navigational status at the mark of the corresponding vessel on the graphical position display when the processor obtains through radio communication a navigation status of a vessel or a distress/emergency notification.

7. The apparatus for displaying other ship targets according to claim 2, further comprising:
   a memory for storing vessel information for a certain period of time;
   wherein when a specific vessel is selected with the human/machine interface, the display is configured to display the ship trail of the corresponding specific vessel on the graphical position display.

* * * * *